United States Patent [19]
Dori et al.

[11] Patent Number: 4,866,053
[45] Date of Patent: Sep. 12, 1989

[54] METHOD OF TREATING A BURN EMPLOYING A METALLO-ORGANIC COBALT COMPOUND

[75] Inventors: Zvi Dori; David Gershon; Yehuda Scharf, all of Haifa, Israel

[73] Assignee: Chai-Tech Corporation, Greenvale, N.Y.

[21] Appl. No.: 147,714

[22] Filed: Jan. 25, 1988

Related U.S. Application Data

[63] Continuation-in-part of Ser. No. 862,804, May 13, 1986, abandoned.

[51] Int. Cl.$^4$ .................. A61K 31/40; A61K 31/295; A61K 31/555
[52] U.S. Cl. .................................... 514/184; 514/420; 514/501; 514/502
[58] Field of Search ................ 514/184, 420, 501, 502

*Primary Examiner*—Stanley J. Friedman
*Attorney, Agent, or Firm*—John P. White

[57] ABSTRACT

A new method of treating a burn is disclosed wherein a cobalt-containing metallo-organic complex is applied to the burn site to promote epithelialization and in some cases hair follicle preservation as well.

12 Claims, No Drawings

METHOD OF TREATING A BURN EMPLOYING A METALLO-ORGANIC COBALT COMPOUND

CROSS REFERENCE TO RELATED APPLICATIONS

This application is a continuation-in-part of Ser. No. 862,804 filed May 13, 1986, now abandoned.

FIELD OF THE INVENTION

This invention relates to a method of treating a burn by employing a cobalt-containing metallo-organic compound.

BACKGROUND OF THE INVENTION

The treatment of burns of the first, second, and third degree, has long been, and remains, one of the most difficult medical problems. The criteria for success of any method for treating a burn include proper contraction of the wound, epithelialization, hair follicle preservation, and the assessment of newly formed granulation tissue.

Contraction represents the difference between the initial wound size of the burn and the size of the burn 12 days later (12th post burn day or PBD), which includes both opened and healed areas calculated as a percentage of the initial wound size.

Epithelialization represents the percentage of the newly covered areas of the burn surface on the 12th PBD out of the total wound area on that same day.

The presence of hair follicles indicates maintenance of dermal microcirculation and prevention of tissue ischemia and thus ischemic and postischemic damage. The preservation of hair follicles and their count should be carried out microscopically in tissue sections.

Also important in evaluation of a medicament for treating burns is the assessment of newly formed granulation tissue. The thickness of the new collagen layer synthesized in the healing burn should be measured on PBD 12.

OBJECTS OF THE INVENTION

It is an object of the invention to provide a new method for treating burns.

It is a further object of the invention to provide the maximum epithelialization of the burn on a macroscopic level.

It is a further object of the invention to provide the maximum hair follicle preservation on a microscopic level.

SUMMARY OF THE INVENTION

We have discovered a new method that is highly effective in the treatment of burns. The method involves direct application of a medicament to the site of the burn. More spcifically the method involves treating a burn in a mammalian subject by topically administering to the affected area, a therapeutically effective amount of a metallo-organic compound selected from the group consisting of:

a cobalt(III)-bis(acetyl or propioacetone)ethylenediimine complex;

[Co (2,3,9,10-tetra(lower alkyl)-1,4,8,11-tetraazacycalotetradeca-1,3,8,10-tetraene)Cl$_2$]Cl; and

[Co (2,12-dimethyl-3,7,11,17-tetraazabicyclo(11.3.1)heptadeca-1(17),2,11,13,15-pentaene)Cl$_2$Cl.H$_2$O.

The preferred group among the abovementioned cobalt-containing complexes is the cobalt(III)-bis(acetyl or propioacetone)-ethylenediimine complexes, especially the diammino chloride complexes.

The preferred cobalt(III)-bis(acetyl or propioacetone)ethylenediimine complexes are the cobalt-(III)-bis(acetyl acetone)-ethylenediimine diammino chloride complex designated as Compound 23 and the cobalt(III)-bis(benzoylacetone)-ethylenediimine diammino chloride complex designated Compound 64.

The preferred [Co (2,3,9,10-tetra(lower alkyl)-1,4,7,11-tetraazacyclotetradeca-1,3,8,10-tetrane)Cl$_2$Cl is the [Co (2,3,9,10-tetramethyl-1,4,7,11-tetraazacyclotetradeca-1,3,8,10-t etraene)Cl$_2$]Cl designated Compound 8.

The compound [Co (2,12-dimethyl-3,7,11,17-tetraazabicyclo(11.3.1)heptadeca-1(17),2,11,13,15-pentaene)Cl$_2$]Cl H$_2$O has been designated Compound 39.

The Compounds 8, 23, 39 and 64 have the following structural formulae:

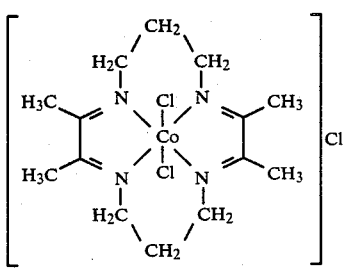

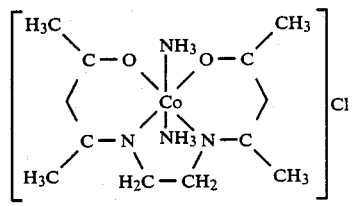

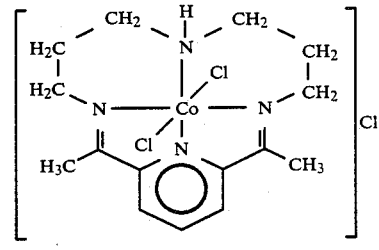

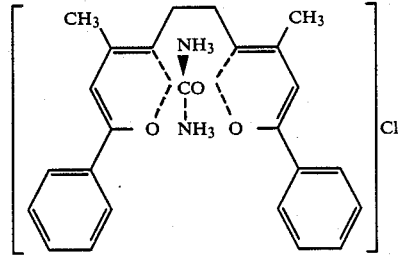

The metallo-organic cobalt complexes of the present invention are water-soluble and may be dissolved in a number of polar, protic solvents such as water or especially normal saline. However, these metallo-organic cobalt complexes may also be suspended in a suspension medium that is not miscible with water, for example petrolatum.

The concentration of the metallo-organic cobalt complex in the solvent or suspension medium can vary from 0.1 to 50 mg/ml. A preferred concentration range lies between 1 and 10 mg/ml.

The metallo-organic cobalt complexes may be applied to the site of the burn in the form of an aerosol, in the form of a salve, ointment, or cream, or directly in a liquid solvent, preferably normal saline, by the use of a medicine dropper. Furthermore the metallo-organic cobalt complexes may be applied to the burn site together with a topical anesthetic agent such as benzocaine, a soothing agent such as menthol, and antibacterial agent such as bacitracin, or a combination of these ingredients.

The following examples are directed to the preparation of the metallo-organic cobalt complexes.

PREPARATION OF THE COMPOUNDS

[Co(Tim)Cl$_2$]Cl - Compound 8)

Tim=2,3,9,10-tetramethyl-1,4,8,11-tetraazacyclotetradeca-1,3,8,10-tetraene

The procedure of Bush et al (Inorg. Chem., 1972, 11, 2893) was employed to prepare [Co(Tim)Cl$_2$]PF$_6$.

A satured solution of tetramethylammonium chloride in acetone was added slowly to a satured solution of [Co(Tim)Cl$_2$]PF$_6$ in acetone until the solution became cloudy. Cooling afforded light green crystals of compound 8.

Anal. Calcd. for C$_{14}$H$_{24}$N$_4$CoCl$_3$: C, 40.63; H, 5.8; N, 13,54. Found: C, 40.57; H, 5.67; N, 13.15.

Cobalt(III) Bis(acetylacetone)-ethylenediimine Complex (Compound 23)

[Co(BAE)NH$_3$)$_2$]Cl

This complex was prepared by a modification of the procedure described by G. Costa et al., J. Organometal, Chem., 1966, 6, 181–187.

Bis(acetylacetone)-ethylenediimine (BAE, 2.24 g. 10 mmol) was dissolved in methanol (100 ml) and treated with cobalt chloride hexahydrate (2.38 g, 10 mmol). The brown solution was stirred at room temperature for 1½ days in order to allow oxidation of the cobalt (not precipitate formed), treated with 7 ml of conc. aq. ammonia solution, and then heated under reflux for 2 hrs. The yellow-brown solid that separated upon standing was recrysted. from ethanol/water (compound 23).

Anal. Calcd. for C$_{12}$H$_{24}$O$_2$N$_4$CoCl C, 41.09; H, 6.90. Found: C, 40.81: H, 7.00.

[Co(CR)Cl$_2$]Cl.H$_2$O (Compound 39)

CR=2,12-dimethyl-3,7,11,17-tetraazabicyclo[11.3.1-]heptadeca-1(17),2,11,13,15-pentaene The Co(II) complex, [Co(CR)Cl$_2$], was prepared and oxidized by the procedure described by Poon et al. for the analogous perchlorate (J. Chem. Soc. Dalton, 1977, 1247–1251). The complex (compound 39) was recrystallized from acetone.

Anal. Calcd. for: C$_{16}$H$_{24}$ON$_4$CoCl$_3$: C, 42.35; H, 5.33; N, 12.35; Cl, 23.45. Found: C, 41.35; H, 5.69; N, 12.07; Cl, 23.64.

Co N,N'-ethylene bisbenzoylacetone-ethylenediimino-diamminocobalt (III) chloride [Co-(bzacen)(NH$_3$)$_2$Cl]C$_{22}$H$_{30}$N$_4$O$_2$CoCl (Compound 64)

Preparation of bisbenzoylacetone-ethylendiiamine

To a solution of 0.5 mole of benzoylacetone dissolved acid and filtered, was slowly added with stirring a solution of 0.25 mole of anhydrous ethylenediamine in 10 cc absolute ethanol.

The stirring was stopped after the addition of the diamine. The Schiff base was readily obtained after cooling of the solution as white crystals which usually did not require recrystallization.

Preparation of the Co(III) complex

To 22 mmole of the ligand dissolved in 100 cc of dichloromethane was added a filtered solution of 20 mmole of CoCl$_2$, 6H$_2$O in 100 cc absolute methanol. The solution was vigorously stirred in an open vessel while a concentrated solution of ammonium hydroxide was added dropwise. a yellow-ochre product was formed and the product was left overnight. The solution was concentrated in an evaporator and filtered to remove some of the unreacted ligand. Brown needles were obtained after evaporation of the mother liquor. The complex is soluble in ethanol, methanol, water, DMF, dichloromethane etc . . . The visible absorption spectrum of aqueous solutions exhibits a peak around 300 nm. The N.M.R. and I.R. spectra of the complex are consistent with the expected formula.

The following examples are directed to the preparation of pharmaceutical composition for the typical treatment of burns.

EXAMPLE I

An aerosol composition is prepared having the following proportions:

| | |
|---|---|
| Benzocaine | 1.00% |
| Camphor | 0.10 |
| Menthol | 0.10 |
| Pyrilamine Malaete | 0.25 |
| Bacitracin | 0.02 |
| Acetulan ® (Acetylated landin alcohols) | 1.00 |
| Oleyl Alcohol | 4.00 |
| Dipropylene Glycol | 1.00 |
| Compound 23 | 0.3 |
| Propellant 152 a/II | 92.23 |
| | 100.00% |

EXAMPLE II

The following water-soluble ointment is prepared having the following proportions:

| Polyethylene Glycol 200 | |
|---|---|
| Monosterate | 15.0% |
| Veegun | 5.0 |
| Polysorbate 80 | 1.0 |
| Methylparaben | 0.1 |
| Compound 23 | 0.3 |
| Purified water | 78.6 |
| | 100.00% |

EXAMPLE III

The following oleaginous ointment is prepared having the following proportions:

| | |
|---|---|
| Compound 64 | .38% |
| Petrolatum balance to 100% | |

Burn Would Healing in the Guinea Pig

Female and male Hartely derived albino guinea-pigs weighing 500–700 gm were used throughout this study. They were housed individually and fed ad libitium normal guinea-pig's chow and water, supplemented with 1 gm of Vitamin C per week.

The back of each animal was clipped and depilated 24 hours prior to the burn inury. Two symmetrical mirror-image round burns were inflicted on the back of each animal with an aluninum template heated to 75° C. and applied for 5 seconds under general anaesthesia (ketamine 150 mg/kg I.M.). Intraortic India ink injection indicated in our preliminary studies that the injuries were deep second-degree burns. The burn areas were dressed in the same fashion as is routinely done in cases of such burns.

Treatments: Application of drugs was carried out as follows: 5 times a day for the first four days and twice daily from the fifth to the 12th day. On day twelve the animals were sacrificed and the wound tissues were sent for histological examination.

Control wounds were treated with 1 mg bovine serum albumin/1 ml saline or with 1 ml of saline only. Catalase treatment was also applied in 1 mg/ml saline. Compound 23 was applied at either 3 mg/ml or varying concentrations of 3 mg/ml for the first four days, 2 mg/ml twice daily from the 5th to the 8th day and 1 mg/ml twice daily from the 9th to the 12th day.

Mode of treatment: The wounds were selected for treatment at random. Three or four treatment groups were performed in each experiment. All dressings were changed under general anaesthesia every four days, at which time wound tracing for healing analysis was performed.

Evaluation of Healing

The evaluation is based upon the following four criteria:

1. Epithelialization—wound epithelialization expressed as percent was calculated employing the following formula:

$$E_1 = \frac{A12 - Ao}{A12} \times 100$$

where
$E_1$ = rate of epithelialization expressed in percent.
$A12$ = wound size on the 12th day post burn.
$Ao$ = area of open wound on the same 12th day.

2. Contraction—The burn wound size as delineated by its outer boundaries was traced on a transparent polyethylene sheet on post burn days (PBD) 4, 8 and 12. Areas were measured by a system composed of an IBM PC computerized video-camera interfaced with especially designed software. The percentage of contraction was calculated according to the following formula $$C = \frac{A_1 - A_{12}}{A_1} \times 100$$

where:
C—percentage of contraction on PBD 12.
$A_1$ = initial burn wound size.
$A_{12}$—burn wound size on PBD 12 (opened and healed wound).
Excessive contraction leads to varying degrees of limitation of use of healed areas and is thus unfavorable.

3. Assessment of the newly formed granulation tissue—Since the evaluation of collagen synthesis is precluded in burn wound models, the newly formed granulation tissue in each burn wound was assembled histologically on PBD 12. Four adjacent sections were taken from the center of each wound. Employing the Mason's Trichrome staining method aided to delineate the newly formed granulation tissue which originated from the non-burned dermal layer in each section.

4. Hair follicle count—The preservation of hair follicles and their count was quantified. The presence of hair follicles and their regeneration indicated preservation of blood circulation and the degree of healing of the underlying tissues of the dermis.

RESULTS

1. Epithelialization (E1) (for tables 1, 2) is clearly superior in the wounds receiving Compound 23 treatment being 50.1% to 8.14% for various Compounds 23 concentrations, as compared with the average of 36.2% of the (34.4% and 38.6% accordingly) control wounds which were treated with either BSA or saline only. Catalase treatment prevented new epithelial formation almost completely - and most of the wound remained unhealed.

2. Contraction—is a natural process occurring in each healing wound and too much contraction during healing may cause organ dysfunction. The results in tables 1, 2 indicate that Compound 23 particularly in the higher concentration did not enhance contraction and may actually somewhat reduce this process.

3. Granulation tissue formation—In the five control wounds and three Compound 23 treated wound analyzed from experiment no. 3, the thickness of the newly formed collagen in controls was 539 mm$^2$ on the average whereas in Compound 23 treated wounds it was 467 mm$^2$. This constitutes 86% of the collagen formed in untreated healing indicating that Compound 23 does not cause and may reduce fibrosis. This means that the compound reduces the amount of scar tissue and allows more normal tissue to be formed in the treated wounds.

4. Hair Follical Count—The presence of hair follicles indicates maintenance of dermal microcirculation and prevention of tissue ischemia and thus ischemic and postischemic damage. The preservation of hair follicles and their count were undertaken; the number of regenerated hair follicles were counted microscopically in tissue sections. The biological section was projected onto a video, colored screen, connected to a color camera. Hair follicles were counted in each wound, in three to eight microscopic fields, in each of 4-8 histological sections. Each field was 2 mm long and 5 microns thick. The mean and standard error (SE) were calculated for each wound and for the whole treatment group. See especially Tables 1a, 1b and 1c which appear hereinafter.

TABLE 1

| experiment no. 3 (10 animals - 20 wounds) | | | |
|---|---|---|---|
| | Epithelialization-% | | |
| | E1 | E2 | Contraction-% |
| control | 34.4 | 21.3 | 35.8 |
| Compound 23 3 mg/ml | 50.1 | 31.7 | 35.7 |
| catalase | 6.1 | 2.8 | 41.4 |

TABLE 2

| experiment no. 4 (11 animals - 22 wounds) | | | |
|---|---|---|---|
| | Epithelialization-% | | |
| | E1 | E2 | Contraction-% |
| control | 38.6 | 22.5 | 40.1 |
| Compound 23 3 mg/ml | 81.4 | 51.6 | 37.5 |
| compound 23 3/2/1 mg | 61.3 | 33.6 | 42.1 |

Epithelialization -E1 represents the % of the newly covered area out of the total wound area on the 12th day. E2- represents the % of the healed area on the 12th day out of the total area of the primary wound induced at zero time.

In the subsequent experiment we used 20 guinea pigs and inflicted 32 wounds. 14 control wounds were treated with saline. 9 wounds were treated with Compound-64 (3.8 mg/ml). 9 wounds were treated with Compound-23 3 mg/ml.

Table 3 summarizes the results of this experiment, with respect to % epithelialization and %contraction.

TABLE 3

| | experiment no. 5 | |
|---|---|---|
| | % Epithelialization = E1 | % Contraction |
| control | 69.2* | 44.4 |
| Compound-64 3.8 mg | 97.3** | 42.1 |
| Compound-23 | 91.3** | 37.0 |

*higher control values over previous experiments due to changed frequency of application of dressings
**virtually total recovery With respect to epithelialization the two compounds 23 and 64 show considerable improvement as compared to untreated. Contraction was not significantly changed by the treatments.

The following tables 1a, 2a and 3a each summarizes all the parameters which were assessed for experiments #3, #4, #5 respectively.

There was no substantially significant difference in the initial wound size among the treatment groups of each experiment as should be expected (Tables 1, 2, 3 and 1a, 2a and 3a respectively).

Contraction

Contraction was not significantly different among the various treatment groups in experiments #3 and #4. However, in experiment #5 contraction was very significantly lower in the Co-BAE-23 treated group as compared to controls (tab. 3).

Conclusion

Contraction is a natural process occurring in each healing wound. Thus, excessive contraction may lead to varying degrees of organ limitation and is thus unfavorable. Contraction with the various treatments given and especially with the Co-BAE-23 did not exceed control values and was actually reduced in experiment #5. This indicates that the drug does not heal by producing excessive fibrosis. A fibrotic scar is less aesthetic and limits the functional capacity of the healed area.

Epithelialization

In experiment #3 (Tab 1a) epithelialization was only 6% in catalase treated group, 34.4% for control-BBA treated wound and 50% for Co-BAE-23. Although epithelialization with Co-BAE-23 treatment was superior to control treated wounds, it was not statistically significant. Thus catalase treatment was significantly worse than the control or Co-BAE-23 treatments.

In experiment #4 (tab 2a) treatment with 3mg of Co-BAE-23 significantly improved epithelialization to 89% as compared with 38.5 in control treated wounds. The use of decreasing amounts of Co-BAE-23 (treatment C) also improved epithelialization, but to a lesser degree.

In experiment #5 (tab 3a) the wound dressings were not changed on the 4th day, but only on the 8th and 12th PBD. The reduced dressing in experiment #5 resulted in improved healing of the wounds of all groups compared with experiments #3 and #4. Epithelialization with 3mg of Co-BAE-23 was 90.3%, meaning that wounds were almost completely healed on day 12. Another Co compound was introduced. Co-BRAE-64 and it also dramatically improved epithelialization to 97%.

Conclusion

Across the three experiments reported here, epithelialization was superior in all the groups treated with Co compounds. This should be considered in light of the crucial role of epithelialization in the process of healing.

Hair Follicle Formation

Hair follicle preservation and formation is very crucial in the assessment of wound healing since, it also indicates the maintenance of dermal microcirculation and prevention of tissue ischemia.

Hair follicle preservation in experiment #3 (table 1a) was very significantly better in Co-BAE-23 than either catalase or control treated groups, the amount of hairs per field was twice as much in the Co-BAE-23 treated group: 15.5 in Co-BAE-23 vs. 8.2 and 9.2 in control and catalase treatments respectively.

Experiment #4 (table 2a) exhibited the same phenomenon, 3 mg of Co-BAE-23 and decreasing amounts of Co-BAE-23 were superior to the control group, though treatment with higher Co-BAE-23 amounts was superior to decreasing amounts of the same treatment i.e. 15.4 and 13.1 hair follicles per field of Co-BAE-23 treated groups respectively vs 6.9 hair follicles for control. In tab. 3a (exp #5) Co-BAE-23 proved again superior to the control. Although very surprisingly the other Co-Compound, Co-BBAE-64, which proved to be an inducer of epithelialization, did not induce hair follicle preservation over control values, and was significantly lower than treatment with Co-BAE-23.

Conclusion: Across the three experiments reported here Co-BAE-23 proved superior with respect to hair follicle preservation which coincided with superior epithelialization, which respresents healing on a macroscopic level. Hair follicle preservation was two fold higher than control or any other treatment suggesting indeed that microcirculation injury and ischemia resulting from superoxide radical production were at least partially prevented by the use of Co-BAE-23 as superoxide radical scavenger.

Newly Formed Granulation Tissue—The thickness of the newly formed granulation tissue on PBD 12 was not fully assessed but in both experiments 3 and 4 (tab. 1a, 2a) the collagen formed in the Co-BAE-23 treated group was slightly thicker (10% to 15%) than control values but was not statistically significant. The fact that the layer of new collagen did not exceed that of control by more than 10% to 15% taken together with the fact that contraction was lower due to treatment indicates that a more aesthetic scar will result from our treatment with Co-BAE-23.

Concluding Remarks

The data indicate that burn wound healing in this guinea pig model was significantly accelerated in the groups treated especially with Co-compounds i.e. Co-BAE-23 and Co-BBAE-64. This improvement was accompanied by a significant increase in epithelialization. Moreover, the Co-BAE-23 also demonstrated improved hair follicle preservation, a fact which indicates that the microcirculation in the burn area was at least partially protected and therefore regenerated better during the healing process. The fact that contraction and new granulation tissue did not increase by Co-BAE-23 indicates that the scar tissue will not become excessively fibrotic and thus will result in a more aesthetic scar and a more functional healing organ.

TABLE 1a

Assessment of burn wound healing by means of contraction, epithelialization, hair follicle preservation, and newly formed granulation tissue.

exp. 3
Female guinea pigs = 10, wounds (n) = 20
Weight = 530 + 10 gr.
Treatments:  A (n = 6) catalase        1 mg/ml/treatment
             B (n = 7) BBA = control   1 mg/ml/treatment
             C (n = 7) Co-BAE-23       3 mg/ml/treatment

| Treatment | A Catalase | B BBA = control | C Co-BAE-23 |
|---|---|---|---|
| Initial wound size - mm$^2$ | 1249.13 + 25.64 | 1283.4 + 68.7 | 1267 + 37.94 |
| Contraction PBD-12(%) | 41.47 + 4.73 | 35.83 + 4.04 | 35.71 + 2.42 |
| Epithelialization PBD-12(%) | 6.05 + 6.05 | 34.4 + 11.50 | 50.06 + 12.14* |
| Hair follicles per 2 mm × 5 | 9.25 + 3.3 | 8.18 + 2.15 | 15.5 + 1.38** |
| Hair follicles % of control | 113.4 | 100 | 189** |
| New collagen | not assessed | 654.6 + 16.0 | 730.72 + 44.6 |

* = some statistical significance from control
** = very significant difference from control

TABLE 2a

Assessment of burn wound healing, by means of contraction, epithelialization, hair follicle preservation, and newly formed granulation tissue exp. 4
Male animals = 11, wounds (n) = 22
Weight = 602.7 + 24 gr.
Treatments:
  A (n = 8) Co-BAE-23        3 mg/ml/treatment
  B (n = 7) control - saline 1 ml/treatment
  C (n = 7) Co-BAE-23        3 mg/ml/treatment 1-4 PBD
                             2 mg/ml/treatment 5-8 PBD
                             1 mg/ml/treatment 9-12PBD

| Treatment | A Co-BAE-23 3 mg | B Saline control | C Co-BAE-23 3/2/1 mg |
|---|---|---|---|
| Initial wound size - mm$^2$ | 1466.23 + 77.08 | 1435.74 + 53.19 | 1566.13 + 105 |
| Contraction PBD-12(%) | 36.14 + 2.89 | 40.08 + 1.88 | 42.13 + 2.94 |
| Epithelialization PBD-12(%) | 89.25 + 5.38** | 38.55 + 11.60 | 52.56 + 16.21* |
| Hair follicles per 2 mm × 5 | 15.4 + 0.9** | 6.9 + 2.06 | 13.1 + 2.72* |
| New collagen | 616.6 ± 46 | 576.5 ± 22.3 | 675.3 ± 79 |

* = some statistical significance from control
** = very significant difference from control

TABLE 3a

Assessment of burn wound healing, by means of contraction, epithelialization, hair follicle preservation, and newly formed granulation tissue.

exp. 5
Female animals = 20, wounds (n) = 32
Weight = 532.5 + 6.02 gr.
Treatments:  A (n = 9) Co-BBAE-64       3.0 mg/ml/treatment
             B (n = 14) control - saline 1 ml/treatment
             C (n = 9) Co-BAE-23        3 mg/ml/treatment

| Treatment | A BBAE-64 | B Saline control | C Co-BAE-23 |
|---|---|---|---|
| Initial wound size - mm$^2$ | 1384.76 ± 35.7 | 1398 ± 34.1 | 1294.0 ± 33.9 |
| Contraction PBD-12(%) | 42.03 ± 1.89 | 44.89 ± 3.01 | 38.4 ± 3.17** |
| Epithelialization PBD-12(%) | 97.29 ± 1.51** | 69.25 ± 4.5 | 90.3 ± 5.33** |
| Hair follicles per 2 mm × 5 | 9.9 ± 0.83** | 10.6 ± 1.25 | 15.3 ± 2.39** |
| Hair follicles % of control | 93.4 | 100 | 144** |
| New collagen | not assessed | not assessed | not assessed |

** = very significant difference

We claim:

1. A method of treating a burn in a mammalian subject which comprises the step of topicallly administering to the affected area of the mammalian subject a therapeutically effective amount of a metallo-organic compound selected from the group consisting of:
a cobalt(III)-bis(acetyl or propio acetone)-ethylene -diimine complex;
[Co (2,3,9,10-tetra(lower alkyl)-1,4,8,11-tetraaza cyclotetradeca-1,3,8,10-tetraene)Cl$_2$]Cl; and
[Co (2,12-dimethyl-3,7,11,17-tetraazabicyclo(11.3.1) -heptadeca-1(17),2,11,13,15-pentaene(cl$_2$]Cl.H$_2$O.

2. The method of treating a burn in a mammalian subject defined in claim 1 wherein the metallo-organic compound is a cobalt(III)-bis(acetyl or propio acetone)- ethylenediimine diammino chloride complex.

3. The method of treating a burn in a mammalian subject defined in claim 2 wherein the metallo-organic compound is a cobalt(III)-bis(acetylacetone)-ethylenediimine diammino chloride complex.

4. The method of treating a burn in a mammalian subject defined in claim 2 wherein the metallo-organic compound is a cobalt(III)-bis(benzoylacetone)-ethylenediimine diammino chloride complex.

5. The method of treating a burn in a mammalianm subject defined in claim 1 wherein the metallo-organic compound is either dissolved in a solvent or suspended in a suspension medium.

6. The method of treating a burn in a mammalian subject defined in claim 5 wherein the concentration of the metallo-organic compound dissolved in the solvent or suspended in the suspension medium is 0.1 to 50 mg/ml.

7. The method of treating a burn in a mammalian subject defined in claim 6 wherein the concentration of the metallo-organic compound dissolved in the solvent or suspended in the suspension medium is 1 to 10 mg/ml.

8. The method of treating a burn in a mammalian subject defined in claim 5 wherein the solvent is normal saline.

9. The method of treating a burn in a mammalian subject defined in claim 5 wherein the suspension medium is petrolatum.

10. The method of treating a burn in a mammalian subject defined in claim 5 wherein the metallo-organic compound is applied to the burn in aerosol form.

11. The method of treating a burn in a mammalian subject defined in claim 5 wherein the metallo-organic compound is applied to the burn in the form of a salve, ointment or cream.

12. The method of treating a burn in a mammalian subject defined in claim 5 wherein the metallo-organic compound is applied to the burn together with an anesthetic agent, soothing agent, antibacterial agent, or a combination of these agents.

* * * * *